United States Patent [19]

Gloger et al.

[11] Patent Number: 4,460,683

[45] Date of Patent: Jul. 17, 1984

[54] SOLUBLE LIVER URICASE WITH A PROCESS FOR THE PREPARATION THEREOF AND WITH THE USE THEREOF

[75] Inventors: Manfred Gloger, Weilheim; Josef Heinle, Munich; Helmut Schlumberger, Polling, all of Fed. Rep. of Germany

[73] Assignee: Boehringer Mannheim GmbH, Mannheim, Fed. Rep. of Germany

[21] Appl. No.: 394,562

[22] Filed: Jul. 2, 1982

[30] Foreign Application Priority Data

Jul. 7, 1981 [DE] Fed. Rep. of Germany ....... 3126759

[51] Int. Cl.³ .................... C12Q 1/62; C12N 11/02; C12N 11/10; C12N 11/08; C12N 11/06
[52] U.S. Cl. ..................................... 435/10; 435/177; 435/178; 435/180; 435/181
[58] Field of Search ................. 435/191, 10, 177, 178, 435/180, 181

[56] References Cited

U.S. PATENT DOCUMENTS 3,625,827 12/1971 Wildi et al. .................... 435/180 X
4,273,874 6/1981 Nakanishi et al. ................. 435/191

FOREIGN PATENT DOCUMENTS 135590 10/1980 Japan .................................. 435/229

*Primary Examiner*—Lionel M. Shapiro
*Attorney, Agent, or Firm*—Felfe & Lynch

[57] ABSTRACT

The present invention provides liver uricase, wherein it is covalently bond to a water-soluble polysaccharide, polyacid anhydride, polyvinylpyrrolidone or acid anhydride as carrier substance and is still soluble at pH values below 6.

The present invention also provides a process for the preparation of this liver uricase.

8 Claims, No Drawings

SOLUBLE LIVER URICASE WITH A PROCESS FOR THE PREPARATION THEREOF AND WITH THE USE THEREOF

The present invention is concerned with a liver uricase which is soluble at low pH values, with a process for the preparation thereof and with the use thereof for the determination of uric acid.

Uricase is an enzyme which is widely distributed in the animal kingdom and occurs especially in animal livers. It catalyses the oxidation of uric acid in the presence of oxygen to give allantoin, hydrogen peroxide and carbon dioxide according to the following equation:

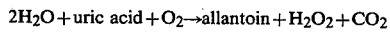

$$2H_2O + \text{uric acid} + O_2 \rightarrow \text{allantoin} + H_2O_2 + CO_2$$

On the basis of the above reaction, uricase should be well suited for the determination of uric acid since one of the reaction products, namely hydrogen peroxide, can be determined by well known methods for this purpose. However, an important disadvantage of liver uricase is that the enzyme is only soluble to relatively high pH values, normally of from pH 9 to 11. Therefore, it is difficult to couple the reaction catalysed by liver uricase with other reactions, for example, such as are necessary for the enzymatic determination of the hydrogen peroxide formed, since, as a rule, substantially neutral pH values are necessary for this purpose.

Uricase are admittedly known which are also sufficiently soluble at a neutral pH value but these must be obtained from micro-organisms, such as *Candida utilis* or *Aspergillus flavus*, and are, therefore, much more expensive, which considerably limits their use for analytical purposes. This also applies to an acid uricase from Streptomyces described in European Patent Specification No. 0012446.

Therefore, it is an object of the present invention so to change the enzyme which is readily obtainable from liver, which can be dissolved out from, for example, pig liver at pH values above 9, that the above-mentioned disadvantages are overcome and the enzyme can also be used in a neutral or acidic medium.

Thus, according to the present invention, there is provided a liver uricase, wherein it is covalently bound to a water-soluble polysaccharide, polyacid anhydride, polyvinylpyrrolidone or acid anhydride as carrier substance and is still soluble at pH values below 6.

The present invention is based upon the surprising fact that a liver uricase which is bound to a water-soluble carrier substance of the mentioned kind is, without substantial alteration of the other properties, outstandingly soluble not only at neutral pH values but also in the acidic range. Thus, preparations according to the present invention are even soluble at pH values of from 1 to 11.

Furthermore, we have ascertained that the enzyme modified according to the present invention is not only soluble at pH values of down to 5.0 but is also active and, for example, at pH 7.0 still displays about 40% of the activity measured at its pH optimum value of 9.5. Thus, it is outstandingly useful for the determination of uric acid in a neutral medium.

Generally, native liver uricase only goes into solution at pH values of 9.5 and higher and, at pH values below 9.0, again precipitates out of solution. However, in the form modified according to the present invention, the solubility is retained down to a pH value of 1. The liver uricase according to the present invention can easily be differentiated from all known uricases on the basis of this property. Furthermore, it is noteworthy that the liver uricase modified according to the present invention maintains its immunological properties unchanged and, therefore, even in its carrier-bound form can be recognised immunologically as liver uricase and can be differentiated from uricases of other origin.

It is known that the properties of enzymes can be changed by carrier fixing. Thus, a change of the activity, a displacement of the pH optimum and a change of the Michaelis constant, of the specific activity and of the stability of enzymes have been described. However, it was not known that, by binding to soluble carriers, the solubility properties of an enzyme can be so drastically changed as is the case with the product according to the present invention. From Enzyme, 26, 49–53/1981, it is known to bind a yeast uricase (from *Candida utilis*) to polyethylene glycol to give a soluble product which has been investigated with regard to its immunological properties. However, a change of the solubility was not reported.

Polysaccharides are preferred as soluble carrier substances according to the present invention, a water-soluble dextran being especially preferred. However, very good results have also been achieved with other soluble polysaccharides, such as, in particular, soluble starch, sugars and sythetic sugar polymers. Amongst the sugars, the saccharides, such as saccharose, have, in turn, proved to be especially useful. High molecular weight polymers of mono- and disaccharides, such as are obtained, for example, by reaction with epihalohydrins, are also highly suitable and are included with the polysaccharides within the scope of the present invention.

However, the carrier substances are not limited to polysaccharides since acid anhydrides, polyacid anhydrides and polyvinylpyrrolidone can also be used. An example of an appropriate acid anhydride is succinic anhydride and an example of an appropriate polyanhydride is a co-polymer of methyl vinyl ether with maleic anhydride. Succinimide derivatives can also be used.

The Michaelis constant $K_M$ and the maximum velocity $V_{max}$ are somewhat changed in the enzyme modified according to the present invention in comparison with native liver uricase. We have found that this change is, to a certain extent, dependent upon the molecular weight of the carrier substance. The $K_M$ values are thereby scarcely influenced, whereas the $V_{max}$ is reduced inversely proportionally to the molecular weight of the carrier. However, especially in the case of high molecular weight carrier materials, such as starch and dextran, the molecular weight should be at least 1000.

The molecular weight of the liver uricase modified according to the present invention depends upon the molecular weight of the carrier material. Thus, for an enzyme modified with dextran T 10, a molecular weight of from 180,000 to 200,000 was ascertained, whereas in the case of dextran T 40, the molecular weight was found to be from 350,000 to 500,000, the molecular weight determinations being carried out by gel chromatography in citrate buffer (pH 5.8). The molecular weight of native liver uricase cannot be determined under these conditions because of its insolubility.

The Michaelis constant $K_M$ and the maximum velocity $V_{max}$ were determined for native uricase and for uricase bound to the two above-mentioned dextran carrier materials, the results obtained being as follows:

|                | $K_M$ [M]           | $V_{max}$ [U/mg. protein] |
|----------------|---------------------|---------------------------|
| native uricase | $3.17 \times 10^{-6}$ | 10.5                      |
| uricase/dex. T10 | $5.0 \times 10^{-6}$  | 5.6                       |
| uricase/dex. T40 | $3.17 \times 10^{-6}$ | 3.7                       |

The liver uricase modified according to the present invention can no longer be precipitated with ammonium sulphate but can be readily precipitated with acetone, the acetone precipitation being reversible, with maintenance of the activity. Therefore, it is also especially useful for the isolation of the carrier-bound enzyme according to the present invention.

The temperature stability of the enzyme at higher temperatures (60° C.) is substantially better than in the case of the native enzyme. Whereas the latter, after 200 minutes at this temperature, only displays 5% of the initial activity, the enzyme according to the present invention still has an activity of 82% after the same period of time. After 240 minutes at 60° C., the native enzyme is inactive, whereas the enzyme according to the present invention still has 79% of its initial activity.

The enzyme according to the present invention can be prepared in known manner by reacting the uricase in aqueous solution with the dissolved carrier material which contains at least one group capable of reaction with $NH_2$ groups, the reaction being carried out at a pH value of from 9 to 11.

Especially good results have been achieved with carrier substances which carry OH groups activated with cyanogen bromide or cyanuric chloride. The coupling is preferably carried out at a temperature of from 0° C. to ambient temperature but higher or lower temperatures can also be used. The coupling preferably takes place at a pH value of from 10.0 to 11.0.

However, other known methods of enzyme fixing can also be used.

In order to achieve the highest possible activity yield, it has proved to be advantageous so to choose the molar ratios of enzyme to carrier molecules that only a relatively small proportion of the $NH_2$ groups of the enzyme are modified. This applies especially in the case of low molecular weight carrier materials. The amount ratio which is appropriate for any particular case can easily be ascertained by preliminary experiments with differing amounts of carrier, on the basis of the activity yields achieved in each particular case.

After conclusion of the coupling reaction, the enzyme according to the present invention can be precipitated, for example, by the addition of acetone and thus isolated. Preferably, however, the solution obtained is lyophilised, desirably after previous purification by dialysis. In the case of lyophilising, stabilising agents are preferably added such as are conventionally used when lyophilising enzymes. Saccharose and mannitol, which can be used individually or together, have proved to be especially suitable as stabilising additives for the lyophilising.

Enzyme preparations according to the present invention are, as mentioned hereinbefore, outstandingly useful for the determination of uric acid. Therefore, a reagent according to the present invention for this purpose comprises a soluble liver uricase according to the present invention, a buffer and a system for determining hydrogen peroxide, allantoin or carbon dioxide. It is also possible to measure the take up of oxygen, for example with an oxygen electrode, as a measure of the amount of uric acid present.

The following Examples are given for the purpose of illustrating the present invention:

EXAMPLE 1

(a) Preparation of the enzyme 5 g. Uricase (BM 150746, 30–50 U/ml., 9 to 10 U/mg. protein) are dialysed at 4° C. against 4×2 liters sodium carbonate/sodium bicarbonate buffer (0.1M, pH 10.2), a clear enzyme solution thereby being obtained.

(b) Activation of the dextran

Soluble dextrans obtained from the firm Roth of Karlsruhe (average molecular weights 10,000; 20,000; 40,000 and 500,000) are activated with cyanogen bromide (Merck) at pH 10.6.

For this purpose, 30 g. of dextran are dissolved in 3 liters of water and the pH adjusted to 10.6 with 2N aqueous sodium hydroxide solution. A total of 9 to 15 g. of cyanogen bromide are added thereto, while stirring, in 3 g. portions in the course of 40 minutes. The pH value is thereby maintained at 10.6, with the help of an autotitrator, by the addition of 2N to 5N aqueous sodium hydroxide solution. The activation reaction is completed when no more sodium hydroxide solution is used up, which is the case after about 1.5 to 2 hours.

A clear solution is then present, the pH value of which is adjusted to 10.0 with 2N hydrochloric acid. The dextran thus activated is adequately dialysed against water at 20° C. within the course of 2 hours.

(c) Binding of the uricase

The previously prepared enzyme solution (a) is combined, while stirring vigorously, with the activated dextran solution (b). Total volume 3.1 to 3.2 liters, pH 10.1 to 10.3. The mixture is then gently stirred for 16 hours at 4° C. or at ambient temperature. After this time, still about 80% of the initial activity is present. The batch has a clear appearance.

(d) Purification of the modified uricase

The modified uricase is subsequently dialysed against 0.04M sodium citrate buffer (pH 5.8) (containing 0.01% sodium azide), the period of dialysis being about 3 hours. Subsequently, 30 g. saccharose and 45 g. mannitol are added to the solution, which is then clarified by filtration, whereafter the solution is lyophilised. 75% of the initial activity are to be found in the lyophilisate.

EXAMPLES 2 TO 12

The process of Example 1 is repeated but with alteration of the conditions and of the carrier materials. The conditions employed and the results obtained are shown in the following Table:

| Example | 2 | 3 | 4 | 5 | 6 |
|---|---|---|---|---|---|
| uricase (mg. protein) | 50 | 50 | 50 | 200 | 500 |
| uricase (activity units) carrier dextran | 360 | 360 | 360 | 1.800 | 5.000 |
| M.W. | 40.000 | 40.000 | 40.000 | 40.000 | 40.000 |
| other | — | — | — | — | — |
| weight ratio carrier:BrCN | 2:1 | 2:1 | 2:1 | 2:1 | 2:1 |
| weight ratio carrier:protein | 2:1 | 4:1 | 8:1 | 4:1 | 6:1 |

| | | | | | |
|---|---|---|---|---|---|
| period (hrs.) | 16 | 16 | 16 | 3 + 13 | 16 |
| temperature °C. | 4° | 4° | 4° | 35° 4° | 4° |
| buffer for lyophilisate | | potassium phosphate, 0.07 M, pH 7.0 | | K. phos., 0.07 M, pH 7.0 | 0.04 M citrate pH 5.8 |
| additives for the lyophilisation | — | — | — | — | saccharose, mannitol |
| yield in g. of lyophilisate | 0.178 | 0.420 | 0.700 | 1.7 | — |
| activity yield % after fixing | 91 | 85 | 68 | 82 | 81 |
| % after lyophilisation | — | — | — | 71 | 77 |
| spec. activity U/mg. lyophilisate | 1.32 | 0.61 | 0.30 | 0.76 | 0.21 |
| stability (residual activity after 3 weeks at 35° C.) | — | — | — | 33% | 100% |

| Example | 7 | 8 | 9 |
|---|---|---|---|
| uricase (mg. protein) | 500 | 100 | 200 |
| uricase (act. in units) | 5.000 | 720 | 1.800 |
| carrier dextran M.W. | 20.000 | — | — |
| other | — | Ficoll 70[(1)] | saccharose |
| activation carrier:BrCN | 2:1 | 2:1 | 2:1 |
| binding carrier:protein | 6:1 | 3:1 | 4:1 |
| period (hrs.) | 16 | 16 | 16 |
| temperature °C. | 4° | 4° | 4° |
| buffer for lyophilisation | 0.04 M citrate pH 5.8 | | potassium phosphate buffer 0.07 M, pH 7.0 |
| additives for the lyophilisation | saccharose mannitol | — | — |
| yields in g. of lyophilisate | — | 0.7 | 1.0 |
| activity yields % after fixing | 70% | 85% | 43% |
| % after lyophilisation | — | — | 36% |
| spec. activity (U/mg. lyophilisate | 0.21 | 0.73 | 0.68 |
| stability (residual activity after 3 weeks at 35° C.) | 100% | — | 51% |

| Example | 10 | 11 | 12 |
|---|---|---|---|
| uricase (mg protein) | 10.000 | 100 | 40.000 |
| uricase (act. in units) | 100.000 | 900 | 40.000 |
| carrier dextran M.W. | 40.000 | 40.000 | 40.000 |
| other | — | — | — |
| activation carrier:BrCN | 2:1 | 5:1 | 2:1 |
| binding carrier:protein | 4:1 | 6:1 | 6:1 |
| period (hrs.) | 16 | 16 | 16 |
| temperature °C. | 4 | 4 | 25 |
| buffer for lyophilisation | 0.04 M Citr. buffer pH 4.8 | 0.04 M Citr. buffer pH 5.8 | 0.04 M Citr. buffer pH 5.8 |
| additives for the lyophilisation | raffinose + mannitol | saccharose + mannitol | saccharose + mannitol |
| yield in g. of lyophilisate | 185 | — | 1.127 |
| activity yields % after fixing | 82 | 90 | 80 |
| % after lyophilisation | 71.5 | — | 69 |
| spec. activity (U/mg. lyophilisate | 0.37 | — | 0.24 |
| stability (residual activity after 3 weeks at 35° C. | 92% | — | 100% |

[(1)] A cane saccharose-epichlorohydrin copolymer, M.W. 70.000

EXAMPLE 13

5 ml. Uricase in glycerol ($\triangleq$ 235 mg. enzyme protein) are introduced into 45 ml. of water and, in an ice-bath, 2×25 mg. succinic anhydride in solid form are added thereto at intervals of 15 minutes. The pH value is kept constant at 9.8 by the addition of a 0.5N aqueous solution of sodium hydroxide, using a titrator, until no more sodium hydroxide solution is utilised. The reaction mixture is then diluted with water to 250 ml. and a further 27 mg. succinic anhydride are added thereto and, at pH 9.8, further titrated as above until the reaction comes to a stop. The activity still amounts to 44%.

The ratio of enzyme protein to succinic anhydride is 3:1. The reaction mixture is subsequently adjusted with 1M citric acid solution to pH 5.5; it remains clear.

Subsequently, there follows a dialysis against 0.04M sodium citrate solution (pH 5.5) containing 0.01% sodium azide. The slight turbidity which appears is centrifuged off. Activity 33%. Lyophilisation after the addition of 1.2 g. saccharose and 1.8 g. mannitol. Lyophilisate: yield 3.7 g.; specific activity 0.178 U/mg.; no loss of activity. Stability: 3 weeks at 4° C.; 100% of the initial activity; 3 weeks at 35° C.: 85% of the initial activity.

EXAMPLE 14

1 ml. Uricase in glycerol ($\triangleq$ 20 mg. enzyme protein) are introduced into 24 ml. of water and mixed in an ice-bath, while stirring, with 25 mg. Gantrez AN 179 (a co-polymer of methyl vinyl ether and maleic anhydride). The pH value is maintained at 9.8 with 0.1N aqueous sodium hydroxide solution, using a titrator, whereafter a further 25 ml. of water are added thereto.

After the reaction has come to a stop, the pH value is adjusted to 5.8 with 1M citric acid solution. The batch remains clear. 60% of the activity is still present. Stability: the activity in the solutions drops to 33% after 16 hours, to 17% after 2 days and to 12% after 4 days, in each case referred to the initial value.

EXAMPLE 15

Example 14 is repeated but with only 6 mg. of Gantrez AN 179. 16 Hours after readjustment of the pH value to 5.8, 48% of the initial activity is still present and after 3 days there is still 38% of the initial activity. After 16 hours, a turbidity can be seen.

EXAMPLE 16

6 g. Dextran T 40 are dissolved in 40 ml. water and cooled in an ice-bath to ±0° C. 600 mg. cyanuric chloride (2,4,6-trichloro-1,3,5-triazine) dissolved in 10 ml. deep-cooled dimethylformamide are then added to the batch. The pH value is adjusted to and maintained at 5.0 by the addition of 0.5N aqueous sodium hydroxide solution.

When the reaction is finished (no further pH change), the activated dextran is purified by reprecipitating three times with, in each case, a two-fold volume excess of deep-cooled acetone. Each time, the acetone precipitate is dissolved in ice water.

The purified dextran can now be used either as a solution or as a lyophilisate for the protein fixing.

For the fixing of the uricase, 1 g. of enzyme protein (as dialysate) in 0.025M sodium bicarbonate/sodium carbonate buffer (pH 10.2) and the activated dextran (aqueous solution) are mixed together and made up to 300 ml. with water. The mixture is subsequently incubated for 16 hours, while stirring. Control of the mixture and lyophilisation:

The batch is adjusted with 1M citric acid solution to pH 5.5 to 5.8 and left to stand for 3 hours at ambient temperature. An opalescence or turbidity must thereby not occur. The clear solution, which contains the fixed enzyme, is, after the addition of 6 g. saccharose and 9 g. mannitol, adjusted to pH 9.0, mixed with 750 mg. ammonium carbaminate and lyophilised. The activity yield is 75 to 80%, referred to the initial activity. Storage for 3 weeks at 35° C. resulted in a reduction of activity by about 30%.

We claim:

1. Liver uricase, wherein it is covalently bound to a water-soluble polysaccharide, polyacid anhydride, polyvinylpyrrolidone or acid anhydride as carrier substance and is still soluble at pH values below 6.

2. Liver uricase according to claim 1, wherein it is soluble at a pH value of from 1 to 11.

3. Liver uricase according to claim 1 or 2, wherein the soluble polysaccharide is a dextran.

4. Liver uricase according to claim 1 or 2, wherein the soluble polysaccharide is soluble starch, sugar or a synthetic sugar polymer.

5. A process for the preparation of a liver uricase covalently bound to a water-soluble polysaccharide, polyacid anhydride, polyvinylpyrrolidone or acid anhydride as a carrier material, and soluble at pH values below 6, comprising the steps of reacting liver uricase in aqueous solution at a pH value of from 9 to 11 with the dissolved carrier material, which contains at least one group capable of reaction with $NH_2$ groups.

6. The process of claim 5, further comprising mixing the solution of carrier-bound uricase obtained from the reaction, with saccharose and/or mannitol, and thereafter lyophilizing the mixture.

7. In the process for the determination of uric acid using liver uricase to form $H_2O_2$ in the measuring reaction, the improvement, wherein use is made of a liver uricase according to claim 1.

8. A process for the determination of uric acid, wherein use is made of a liver uricase according to claim 1.

* * * * *